(12) United States Patent
Driscoll et al.

(10) Patent No.: US 11,495,141 B2
(45) Date of Patent: Nov. 8, 2022

(54) DUAL CHANNEL MEDICAL SIMULATOR

(71) Applicant: CAE HEALTHCARE CANADA INC., Saint-Laurent (CA)

(72) Inventors: Christopher Driscoll, Saint-Laurent (CA); Philippe Villeneuve, Saint-Laurent (CA); Jean-Sebastien Flamand, Saint-Laurent (CA); Giuseppe Mallaci, Saint-Laurent (CA)

(73) Assignee: CAE HEALTHCARE CANADA INC., Saint-Laurent (CA)

( * ) Notice: Subject to any disclaimer, the term of this patent is extended or adjusted under 35 U.S.C. 154(b) by 1105 days.

(21) Appl. No.: 15/940,402

(22) Filed: Mar. 29, 2018

(65) Prior Publication Data
US 2019/0304342 A1 Oct. 3, 2019

(51) Int. Cl.
*G09B 23/28* (2006.01)
*G01D 5/34* (2006.01)
*G01D 5/347* (2006.01)
*A61N 1/372* (2006.01)

(52) U.S. Cl.
CPC .............. *G09B 23/28* (2013.01); *G01D 5/342* (2013.01); *G01D 5/3473* (2013.01); *A61N 1/37205* (2013.01)

(58) Field of Classification Search
CPC ....... G09B 23/28; G01D 5/342; G01D 5/3473
USPC ....................................................... 434/262
See application file for complete search history.

(56) References Cited

U.S. PATENT DOCUMENTS

| 5,917,600 | A | * | 6/1999 | Rongo | ................ | G01B 11/007 |
| | | | | | | 356/622 |
| 9,179,857 | B2 | | 11/2015 | Lee et al. | | |
| 9,204,820 | B2 | | 12/2015 | Clark et al. | | |
| 9,361,808 | B1 | | 6/2016 | Caron | | |
| 9,361,809 | B1 | | 6/2016 | Caron et al. | | |
| 9,364,640 | B2 | | 6/2016 | Vanney et al. | | |
| 2006/0209015 | A1 | * | 9/2006 | Feldmeier | ............ | G06F 3/0317 |
| | | | | | | 345/156 |
| 2007/0273872 | A1 | * | 11/2007 | Vecerina | ................ | A61B 34/76 |
| | | | | | | 356/153 |

(Continued)

FOREIGN PATENT DOCUMENTS

CN 202215882 U * 5/2012
JP S61-190486 A 8/1986
(Continued)

*Primary Examiner* — Kesha Frisby
(74) *Attorney, Agent, or Firm* — Fasken Martineau Dumoulin LLP; Serge Lapointe

(57) ABSTRACT

An apparatus for simulating an insertion of an elongated instrument into a subject, comprising: a frame extending between two end walls along a first axis and two lateral walls along a second axis, one of the two end walls being provided with an insertion aperture and one of the two lateral walls being provided with an insertion hole, the insertion aperture defining a first passageway and the insertion hole defining a second passageway, the first and second passageways intersecting each other at an intersection point; and a sensing unit contained within the frame and configured for measuring at least one of a displacement of the elongated member and a rotation of the elongated member, the sensing unit being positioned adjacent to the intersection point for performing the measurement of the at least one of the displacement and the rotation at the intersection point.

16 Claims, 11 Drawing Sheets

(56) References Cited

U.S. PATENT DOCUMENTS

| | | |
|---|---|---|
| 2013/0030303 A1 | 1/2013 | Ahmed et al. |
| 2014/0349264 A1* | 11/2014 | Shabat .................... G06F 19/00 434/267 |
| 2016/0249817 A1 | 9/2016 | Mazar et al. |
| 2017/0027476 A1 | 2/2017 | Kariv |
| 2017/0065225 A1 | 3/2017 | Hanson |
| 2017/0079546 A1 | 3/2017 | Costello et al. |
| 2017/0087333 A1 | 3/2017 | Sela et al. |
| 2017/0143235 A1 | 5/2017 | Besz et al. |
| 2017/0143305 A1 | 5/2017 | Hiltner et al. |
| 2017/0287632 A1 | 10/2017 | Caron |

FOREIGN PATENT DOCUMENTS

| | | |
|---|---|---|
| JP | H09-187435 A | 7/1997 |
| JP | 2011-045726 A | 3/2011 |
| WO | 2017030435 | 2/2017 |

* cited by examiner

DUAL CHANNEL MEDICAL SIMULATOR

TECHNICAL FIELD

The present invention relates to the field of medical simulators, and more particularly to medical apparatuses for simulating the insertion of a medical instrument into a subject.

BACKGROUND

In order to train medical practitioners to train on medical procedures in which an elongated instrument such a catheter has to be introduced into a human body, simulation system have been developed. Such systems usually comprise a medical simulator into which the catheter has to be introduced and a simulation computer. The medical apparatus tracks the position and/or orientation of the distal end of the catheter and the simulation computer generates images including a representation of the distal end of the catheter according to the measured position and/or orientation.

Usually, the position tracking sensor used for tracking the distal end of the catheter is a mechanical sensor to which the distal end is secured. However, guidewires having a diameter 0.014" to 0.035" for example cannot be tracked because they cannot be secured to the position tracking sensor.

Furthermore, medical simulators are usually cumbersome, thereby preventing the simulation from being easily portable. In addition, medical simulators are usually designed to receive elongated instruments having a diameter comprised within a given range. Therefore, the number and types of elongated instruments that may be used with a medical simulator is limited.

Therefore, there a need for a medical simulator that overcome at least one of the above-identified drawback.

SUMMARY

According a first broad aspect, there is provided a modular apparatus for simulating an insertion of an elongated instrument into a subject, comprising: at least one of: a proximal module comprising a proximal frame extending longitudinally between a first proximal face and a first distal face each provided with a module aperture therethrough; and a distal module comprising a distal frame extending longitudinally between a second proximal face and a second distal face, the second proximal face being provided with a hole therethrough; and a measurement module comprising a measurement frame extending longitudinally between a third proximal face and a third distal face each provided with a measurement aperture, the measurement module being removably securable to at least one of the proximal module and the distal module so that the measurement apertures of the measurement modules and at least one of the module apertures of the proximal module and the hole of the distal module be aligned to form a passageway through which the elongated instrument is insertable; a motion sensing unit contained in the measurement module, the motion sensing unit comprising a processing unit and at least one sensor and being configured for measuring a displacement of the elongated instrument along the passageway; and a communication unit for outputting the measured displacement of the elongated instrument.

In one embodiment, the motion sensing unit is configured for measuring the displacement of the elongated instrument only when a cross-sectional size of the elongated instrument is comprised within a predefined range.

In one embodiment, the motion sensing unit comprises a first sensor for detecting the elongated instrument and measuring the cross-sectional size of the elongated instrument, and a second sensor for measuring the displacement of the elongated instrument In one embodiment, the processing unit is configured for: receiving the measured cross-sectional size from the first sensor; comparing the measured cross-sectional size to the given range; and if the measured cross-sectional size is within the predefined range, activating the second sensor for measuring the displacement of the elongated instrument.

In one embodiment, the first and second sensors are optical sensors.

In one embodiment, the measurement module further comprises a hollow guiding body extending between the measurement holes.

In one embodiment, the hollow guiding body comprises a body aperture for allowing the motion sensing unit to measure the displacement of the elongated instrument.

In one embodiment, the hollow guiding body has a varying cross-sectional dimensional along a portion of a length thereof.

In one embodiment, the proximal module comprises a first hollow body extending between the module apertures for receiving and guiding the elongated instrument therein.

In one embodiment, the distal module comprises a second hollow body extending from the hole for receiving and guiding the elongated instrument therein.

In one embodiment, the measurement module is mechanically securable to at least one of the proximal module and the distal module.

In one embodiment, the measurement module is magnetically securable to at least one of the proximal module and the distal module.

In one embodiment, the apparatus comprises the proximal module and the distal module, the measurement module being removably securable between the proximal and distal modules.

In one embodiment, the proximal module is further removably securable to the distal module.

In one embodiment, the proximal and distal modules are magnetically securable together.

In one embodiment, the proximal and distal modules are mechanically securable together.

In one embodiment, lateral faces of the measurement module are each provided with a respective additional aperture, the additional aperture having a size different than the measurement aperture so that a first elongated instrument having a first cross-sectional dimension be insertable through the measurement apertures and a second elongated instrument having a second and different cross-sectional dimension be insertable through the measurement apertures.

In one embodiment, the motion sensing unit is positioned for measuring a displacement of the first elongated instrument and the measurement module further comprises a displacement sensing unit for measuring a displacement of the second elongated instrument In one embodiment, the measurement apertures define a first path along which the first elongated instrument is movable and the additional apertures define a second and different path along which the second elongated instrument is movable, the motion sensing unit being positioned within the measurement module so as to measure a displacement of the first and second elongated members at an intersection of the first and second paths.

In one embodiment, the measurement module further comprises a hollow structure having a first hollow body extending between the measurement apertures and a second hollow body extending between the additional apertures, the first and second hollow bodies intersecting one another at an intersection section of the hollow structure.

In one embodiment, the intersection section is provided with at least one measurement hole, the motion sensing unit being positioned within the measurement module so as to measure a displacement of the first and second elongated instruments through the at least one measurement hole.

In one embodiment, the motion sensing unit is further configured for measuring a rotation of the elongated instrument.

In one embodiment, the communication unit is contained within the measurement module.

In one embodiment, the communication unit is contained within the proximal module, the proximal module further comprising a processor.

In one embodiment, the proximal module is further provided with a first connector connected to the processor and the measurement module is provided with a second connector connected to the processing unit, the first and second connectors being connectable together upon removably securing the measurement module to the proximal module for transmitting the displacement of the elongated instrument to the processor.

In one embodiment, the apparatus comprises the proximal module and the distal module and further comprising an intermediary module and a sensing module, the measurement module being removably securable to the proximal module and the intermediary module and the sensing module being removably securable to the intermediary module and the distal module, wherein the intermediary module comprises an intermediary frame extending longitudinally between a fourth proximal face and a fourth distal face each provided with an intermediary aperture therethrough; the sensing module comprises a sensing frame extending longitudinally between a fifth proximal face and a fifth distal face each provided with a sensing aperture and a displacement sensing unit contained in the sensing frame, the motion sensing unit comprising a processing unit and at least one sensor and being configured for measuring a displacement of the elongated instrument; and the removable securing of the proximal, measurement, intermediary, sensing and distal modules together allows an alignment of the module apertures of the proximal module, the measurement apertures of the measurement modules, the intermediary apertures of the intermediary module, the sensing apertures of the sensing module and the hole of the distal module to form the passageway through which the elongated instrument is insertable.

In one embodiment, the sensing aperture of the sensing module has a different size than the measurement aperture of the measurement module so that a first elongated instrument having a first cross-sectional dimension be insertable through the sensing aperture of the sensing module and a second elongated instrument having a second and different cross-sectional dimension be insertable through the measurement apertures of the measurement module.

According to another broad aspect, there is provided an apparatus for simulating an insertion of an elongated instrument into a body, comprising: a frame extending along a longitudinal axis between a proximal face and a distal face, the proximal face being provided with an insertion aperture for receiving therein the elongated instrument, the elongated instrument being movable along a path within the frame; a first optical sensor positioned within the frame for measuring a cross-sectional dimension of the elongated instrument; a second optical sensor positioned within the frame for measuring a displacement of the elongated instrument within the frame; and a control unit in communication with the first and second optical sensors and configured for: comparing the measured cross-sectional dimension of the elongated instrument to at least one reference dimension; upon positive comparison, triggering an activation of the second optical sensor; and outputting the measured displacement of the elongated instrument.

In one embodiment, the at least one reference dimension comprises a given dimension.

In one embodiment, the control unit is configured for triggering the activation of the second optical sensor when the measured cross-sectional dimension is greater than the given dimension.

In one embodiment, the control unit is configured for triggering the activation of the second optical sensor when the measured cross-sectional dimension is less than the given dimension.

In one embodiment, the at least one reference dimension comprises two given dimensions forming a predefined dimension range.

In one embodiment, the control unit is configured for triggering the activation of the second optical sensor when the measured cross-sectional dimension is within the predefined dimension range.

In one embodiment, the first optical sensor comprises a light source for emitting a light beam and a light detector for detecting the light beam, the light source and the light detector facing each other on opposite sides of the path so that the elongated instrument at least partially blocks the light beam when inserted between the light source and the light detector.

In one embodiment, the light detector is configured for measuring an optical intensity of the light beam.

In one embodiment, the control unit is configured for comparing the measured optical intensity to at least one reference intensity.

In one embodiment, the at least one reference intensity comprises a given intensity.

In one embodiment, the control unit is configured for triggering the activation of the second optical sensor when the measured optical intensity is greater than the given intensity.

In one embodiment, the control unit is configured for triggering the activation of the second optical sensor when the measured optical intensity dimension is less than the given intensity.

In one embodiment, the at least one reference intensity comprises two given intensities forming a predefined intensity range.

In one embodiment, the control unit is configured for triggering the activation of the second optical sensor when the measured optical intensity is within the predefined intensity range.

In one embodiment, the apparatus further comprises a guiding structure installed within the frame and extending from the insertion aperture for receiving and guiding the elongated instrument.

In one embodiment, the guiding structure comprises a hollow guiding device.

In one embodiment, the hollow guiding device comprising at least one first aperture for allowing the first optical sensor to measure the cross-sectional dimension of the elongated instrument and a second aperture for allowing the second optical sensor to measure the displacement of the elongated instrument within the frame.

In one embodiment, the second optical sensor is further configured for measuring a rotation of the elongated instrument about a longitudinal thereof, the control unit being further configured for outputting the measured rotation of the elongated instrument.

In one embodiment, the second optical sensor comprises a digital image correlation and tracking sensor.

According to a further broad aspect, there is provided an apparatus for simulating an insertion of an elongated instrument into a subject, comprising: a frame defining an enclosure, the frame extending between two ends along a first axis and two lateral walls along a second axis, one of the two end walls being provided with an insertion aperture and one of the two lateral walls being provided an insertion hole, the insertion aperture defining a first passageway within the frame for the elongated instrument and the insertion hole defining a first passageway within the frame for the elongated instrument, the first and second passageways intersecting each other at an intersection point; and a sensing unit contained within the frame and configured for measuring at least one of a displacement of the elongated member and a rotation of the elongated member, the sensing unit being positioned adjacent to the intersection point for performing the measurement of the at least one of the displacement and the rotation at the intersection point.

In one embodiment, the insertion aperture and the insertion hole have different sizes for receiving therein elongated instruments having different cross-sectional dimensions.

In one embodiment, the apparatus further comprises a first guiding structure extending form the insertion aperture along the first passageway for receiving and guiding the elongated instrument inserted through the insertion aperture, and a second guiding structure extending form the insertion hole along the second passageway for receiving and guiding the elongated instrument inserted through the insertion hole.

In one embodiment, the first guiding structure comprises a first hollow guiding device for receiving the elongated instrument therein and the second guiding structure comprises a second hollow device for receiving the elongated instrument therein.

In one embodiment, the first hollow guiding device comprises a first tube and the second hollow guiding device comprises a second tube.

In one embodiment, the first and second hollow guiding devices are transparent.

In one embodiment, the sensing unit comprises at least one camera for imaging the elongated instrument at an intersection of the first hollow guiding device and the second hollow guiding device, the sensing unit being further configured for determining the at least one of the displacement and the rotation using images taken by the at least one camera.

In one embodiment, the first hollow guiding device comprises a first aperture and the second hollow guiding device comprises a second aperture, the first and second apertures forming a sensing aperture located at an intersection between the first hollow guiding device and the second hollow guiding device.

In one embodiment, the sensing unit comprises at least one optical sensor for measuring the at least one of the displacement and the rotation of the elongated instrument.

In one embodiment, the at least one optical sensor comprises at least one digital image correlation and tracking sensor.

In one embodiment, the sensing unit comprises at least one mechanical sensor for measuring the at least one of the displacement and the rotation of the elongated instrument.

In one embodiment, the at least one mechanical sensor comprises a ball rotatably engageable with the elongated instrument and two rotary sensors each for measuring a rotation of the ball about a respective rotation axis.

In one embodiment, each one of the two rotary sensor comprises a roller rotatably connected to the ball and an encode for measuring a rotation of the roller.

In one embodiment, each one of the two rotary sensors comprise an optical sensor.

In one embodiment, the optical sensor comprises a digital image correlation and tracking sensor.

In one embodiment, the at least one mechanical sensor comprises two rollers each rotatably engageable with the elongated instrument and two encoders each for measuring a rotation of a respective one of the two rollers.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

There is described an apparatus that may be used for simulating medical interventions relying on insertion of a medical instrument into an anatomical structure of a patient such as veins, arteries and other tubular anatomical structures. The medical instrument may be a guidewire, a lead wire, a catheter, a delivery tube, or the like. For example, the present apparatus may be used for simulating the implantation of a micro-pacemaker small enough to be delivered with minimally invasive techniques through a catheter, and implanted directly into the heart. Transcatheter pacemaker implantations are generally performed through an opening realized in the femoral artery in the groin region although other entry points may be used. Training of such a procedure may be done as a sequence of procedures, for example an initial guidewire insertion up to the heart, a catheter insertion up to the heart, fine manipulation of the implant inside the heart before final attachment, or as complete procedure encompassing all the manipulations required for a complete implantation process. The present apparatus thus allows training medical professionals on a sequence of procedures of the complete procedure with improved realistic feedback feeling.

The apparatus is configured for tracking the position of the distal end of the medical instrument once inserted into the apparatus. The apparatus is connectable to a computer machine, such as a laptop, that is used for simulating medical images of the subject which are displayed on a display. The simulated images further comprise a representation of the medical instrument according to the position of the distal end of the medical instrument within the apparatus.

Figure 1:
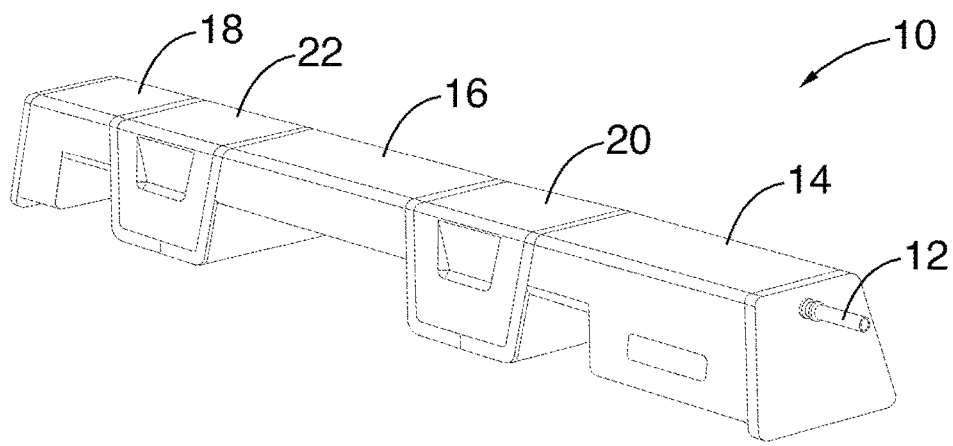
FIG. 1 is a perspective view of a modular medical apparatus for simulating the insertion of an elongated instrument into a subject, the modular medical apparatus comprising a proximal module, a distal module, two sensing modules and an intermediary module removably secured together, in accordance with an embodiment.
Figure 2:
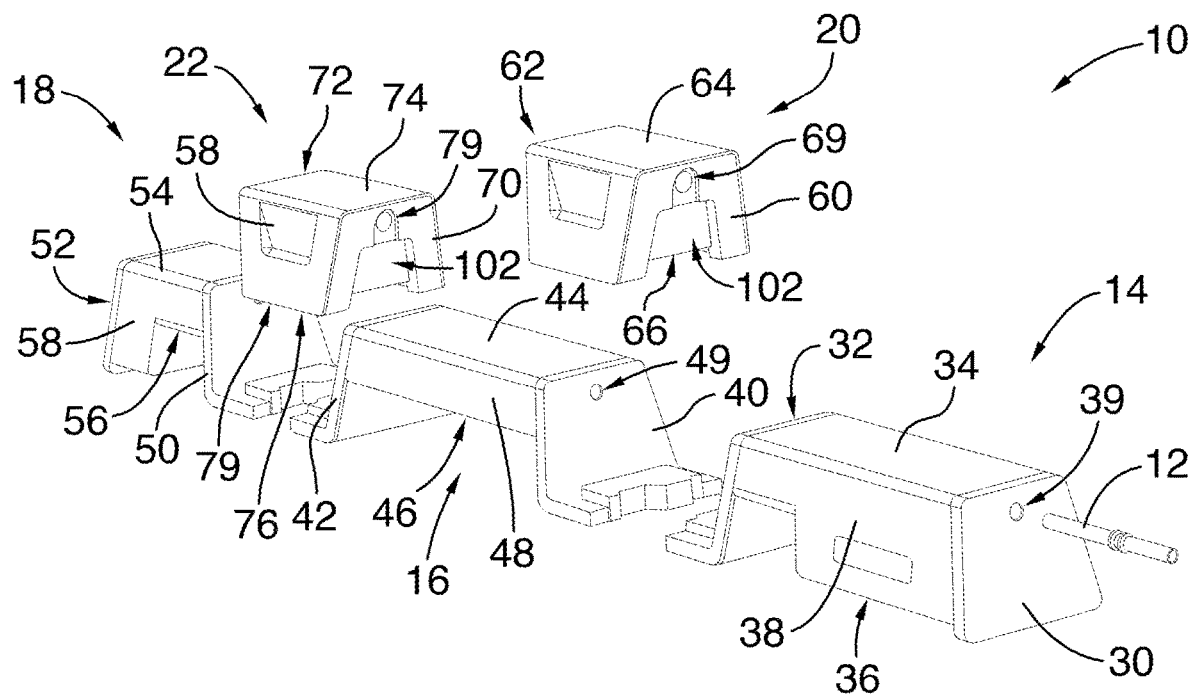
FIG. 2 is a perspective exploded view of the modular medical apparatus of FIG. 1.

FIGS. 1 and 2 illustrate one embodiment of a modular apparatus 10 for simulating an insertion of a medical elongated instrument 12 into a subject. The apparatus 10 may be used for training a medical practitioner to the insertion of the elongated instrument 12 into a subject.

The apparatus 10 comprises a plurality of modules removably connectable together, i.e. a proximal module 14, an intermediary module 16, a distal module 18, a first measurement or sensing module 20 and a second measurement or sensing module 22. As illustrated in FIG. 1, when the modules 14-22 are removably assembled together, the first sensing module 20 is positioned between the proximal module 14 and the intermediary module 16 while the second sensing module 22 is located between the intermediary module 16 and the distal module 18.

As illustrated in FIG. 2, each module 14-22 is independent from one another and can be removed from the assembly. The proximal, intermediary and distal modules 14, 16 and 18 are used for each providing a given length of insertion for the elongated instrument 14 while the sensing modules 20 and 22 are used for measuring the displacement or translation length of the elongated instrument 14 within the apparatus 10. Optionally, the sensing modules 20 and 22 may be further configured for measuring a rotation of the elongated instrument 12 about its longitudinal axis.

The proximal module 14 comprises a frame extending longitudinally between a proximal wall 30 and a distal wall 32 and also comprises a top wall 34 and a bottom wall 36 and two lateral walls 38 which extends between the proximal and distal walls 30 and 32. The proximal and distal walls 30 and 32 are each provided with an aperture 39 sized and shaped for receiving the elongated instrument 12 therein.

The intermediary module 16 comprises a frame extending longitudinally between a proximal wall 40 and a distal wall 42 and also comprises a top wall 44 and a bottom wall 46 and two lateral walls 48 which extends between the proximal and distal walls 40 and 42. The proximal and distal walls 40 and 42 are each provided with an aperture 49 sized and shaped for receiving the elongated instrument 12 therein.

The distal module 18 comprises a frame extending longitudinally between a proximal wall 50 and a distal wall 52 and also comprises a top wall 54 and a bottom wall 56 and two lateral walls 58 which extends between the proximal and distal walls 50 and 52. The proximal and distal walls 50 and 52 are each provided with an aperture 59 sized and shaped for receiving the elongated instrument 12 therein.

The first sensing module 20 comprises a frame extending longitudinally between a proximal wall 60 and a distal wall 62 and also comprises a top wall 64 and a bottom wall 66 and two lateral walls 58 which extends between the proximal and distal walls 60 and 62. The proximal and distal walls 60 and 62 are each provided with an aperture 69 sized and shaped for receiving the elongated instrument 12 therein.

The second sensing module 22 comprises a frame extending longitudinally between a proximal wall 70 and a distal wall 72 and also comprises a top wall 74 and a bottom wall 76 and two lateral walls 78 which extends between the proximal and distal walls 70 and 72. The proximal wall 70 is provided with an aperture 79 sized and shaped for receiving the elongated instrument 12 therein.

When the modules 14-22 are removably secured together as illustrated in FIG. 1, the apertures 39, 49, 59, 69 and 79 are aligned along an axis so that the elongated instrument 12 may be inserted through all of the modules 14-22 from the aperture 39 up to inside the distal module 18.

It should be understood that any adequate means for removably securing the modules 14-22 together may be used. For example, screws may be used.

In one embodiment, the proximal, intermediary and distal modules 14-18 are not directly securable together and are removably secured together via the sensing modules 20 and 22.

In another embodiment, the proximal, intermediary and distal modules 14-18 are directly and removably securable together, i.e. the proximal and intermediary modules 14 and 16 may be removably secured together and the intermediary and distal modules 14 and 18 may be removably secured together. In this case, the first sensing module 20 is further removably secured to the proximal module 20 and/or the intermediary module 16, and the second sensing module 22 is removably secured to the intermediary module 16 and/or the distal module 18.

Figure 3:
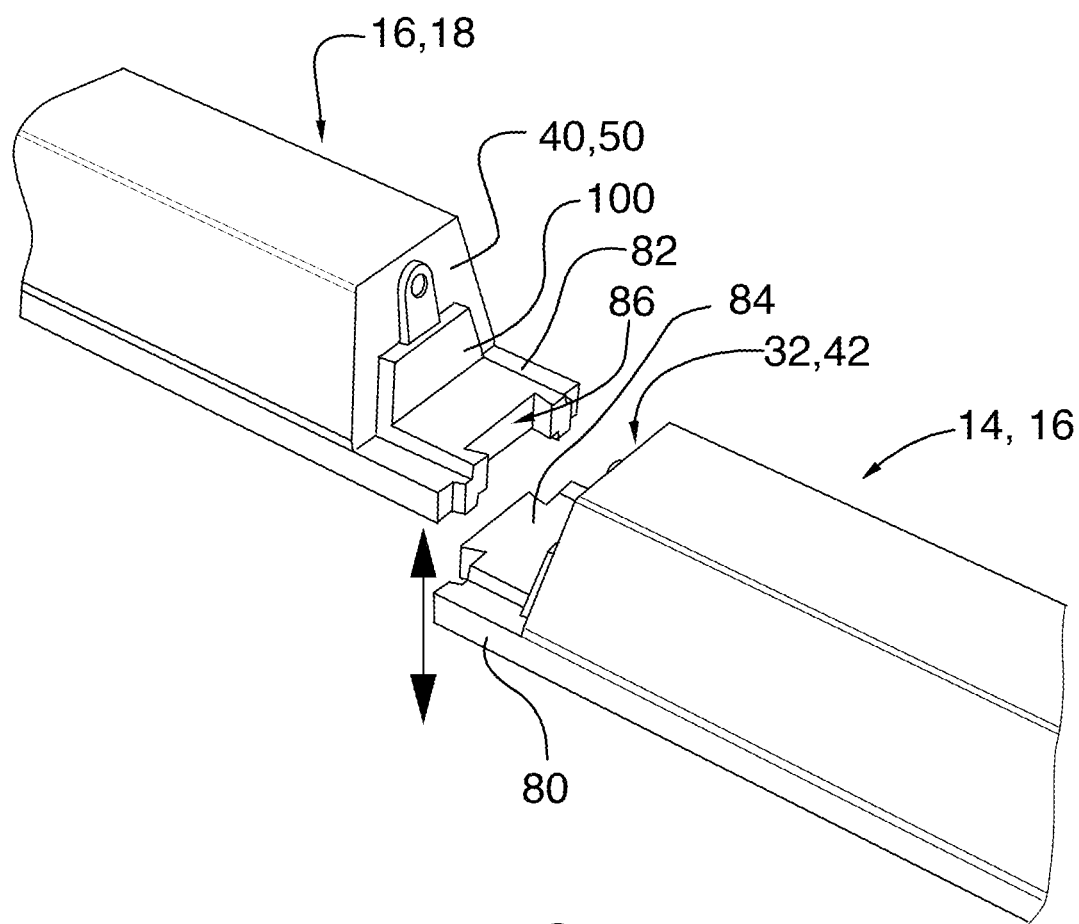
FIG. 3 is a perspective view of two modules mechanically connectable together, in accordance with an embodiment.
Figure 4:
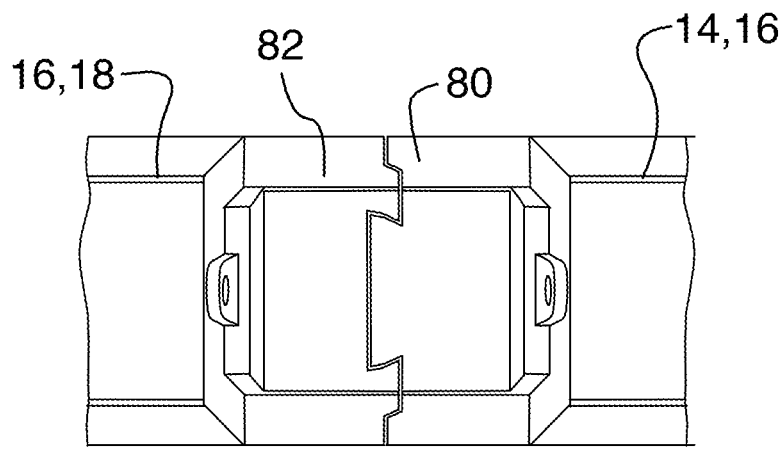
FIG. 4 is a top of the two modules of FIG. 3 once connected together.

FIGS. 3 and 4 illustrates one exemplary mechanical connection for removably connecting together modules 14-18. In this embodiment, the distal wall 32, 42 of the proximal or intermediary module 14, 16 is provided with a first connection plate 80 which extends therefrom adjacent to the bottom wall 36, 46. A second connection plate 82 projects from the proximal wall 40, 50 of the intermediary or distal module 16, 18 adjacent to the bottom wall 46, 56 thereof. The shape of the connection plates 80 and 82 match each other so as to create a mechanical connection. In the illustrated example, the first connection plate 80 is provided with a trapezoidal protrusion 84 and the second connection plate is provided with a trapezoidal recess 86 which mates with the protrusion 84. The modules 14, 16 and 16, 18 are removably secured together by inserting the protrusion 84 into the recess 86. In addition to removably secure the modules 14, 16 and 16, 18 together, the protrusion 84 and the recess 86 allows aligning the modules 14, 16 and 16, 18 so that the apertures 39, 49 and 49, 59 be aligned.

Figure 5:
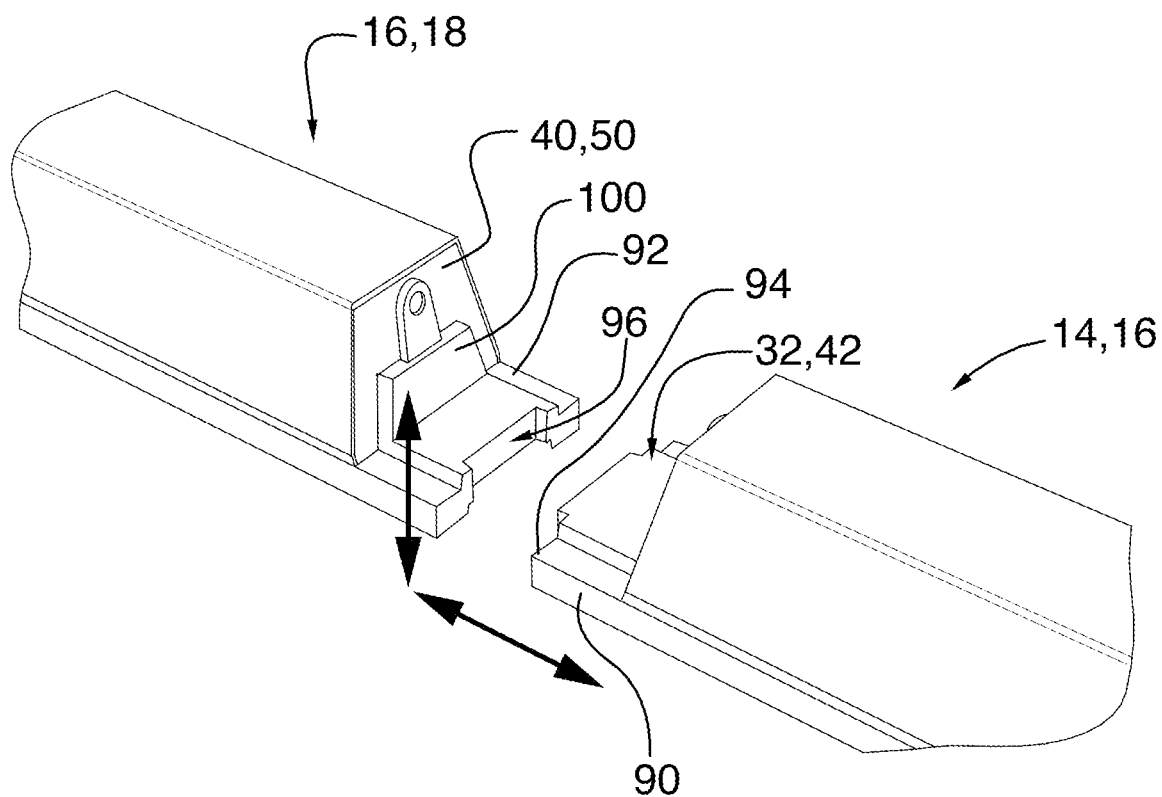
FIG. 5 is a perspective view of two modules magnetically connectable together, in accordance with an embodiment.
Figure 6:
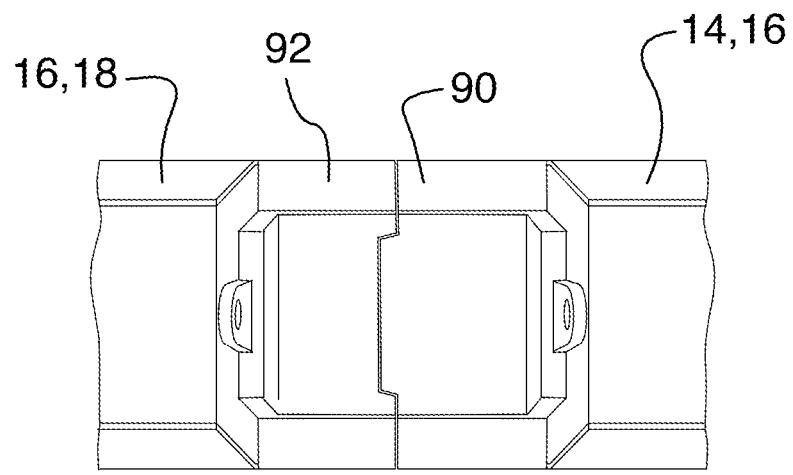
FIG. 6 is a top of the two modules of FIG. 4 once connected together.

FIGS. 5 and 6 illustrates an exemplary magnetic connection for removably securing together the modules 14-18. In this embodiment, the distal wall 32, 42 of the proximal or intermediary module 14, 16 is provided with a first magnetized plate 90 which protrudes therefrom adjacent to the bottom wall 36, 46. A second magnetized plate 92 projects from the proximal wall 40, 50 of the intermediary or distal module 16, 18 adjacent to the bottom wall 46, 56 thereof. The polarity of the magnetized plates 90 and 92 so that they attract each other and thereby removably secure the modules 14, 16 and 16, 18 together. The magnetized plate 90 is provided with an alignment protrusion 94 and the magnetized plate 92 is provided with a mating alignment recess 96. The alignment protrusion and recess 94 and 96 are designed for aligning the modules 14, 16 and 16, 18 so that the apertures 39, 49 and 49, 59 be aligned.

In the illustrated embodiment, the distal wall 32 of the proximal module 14, the walls 40 and 42 of the intermediary module 16 and the proximal wall of the distal module 18 are inclined so that a V-shaped receiving space or recess be present between two adjacent modules 14-16 once the modules 14-18 are removably secured together. The shape and dimension of the frame of the sensing modules 20 and 22 matches these of the V-shaped receiving recess present between two adjacent modules 14-18. For example, the walls 60, 70 and 62, 72 of the sensing module 20, 22 are inclined to match the inclined walls of the modules 14-18. As a result, when the modules 14-18 are removably connected together, two v-shaped recesses are created and a respective sensing module 20, 22 is inserted into each V-shaped recess formed between adjacent modules 14-18. As illustrated in FIG. 1 and once the modules 14-22 have been assembled together, the top walls 34, 44, 54, 64 and 74 are coplanar to form a planar and substantially seamless surface. Similarly, on each side of the apparatus 10, the lateral walls 38, 48, 58, 68 and 78 are coplanar to also form a planar and substantially seamless surface.

In one embodiment, the distal wall 32 of the proximal module 14, the walls 40 and 42 of the intermediary module 16 and the proximal wall of the distal module 18 are each provided with an alignment protrusion 100, as illustrated in FIGS. 3 and 5 for example, and the walls 60, 62 and 70, 72 of the sensing modules 20 and 22 are each provided with a mating recess 102, as illustrated in FIG. 2. The sensing modules 20 and 22 are then aligned with respect to the modules 14-18 by inserting the alignment protrusions 100 of the modules 14-18 into the recesses 102 of the sensing modules 20-22, thereby aligning the apertures of all of the modules 14-22 to allow the translation of the elongated instrument 12 within all of the modules 14-22.

In an embodiment in which the modules 14-18 are provided with magnetized plates 90 and/or 92, the sensing modules 20 and 22 may be provided with two magnets on its bottom wall 66, 76 to magnetically and removably secure the sensing modules 20 and 22 to the modules 14-22.

As mentioned above, the sensing module 20, 22 is configured for measuring the displacement of the elongated instrument within the apparatus 10, and optionally the rotation of the elongated instrument 12 about its longitudinal axis (or the angular position of the elongated instrument 12). It should be understood that any adequate device configured for measuring the displacement of the elongated instrument 112 and optionally the rotation for the elongated instrument 12 may be used and integrated into the sensing modules 20, 22.

Figure 7A:
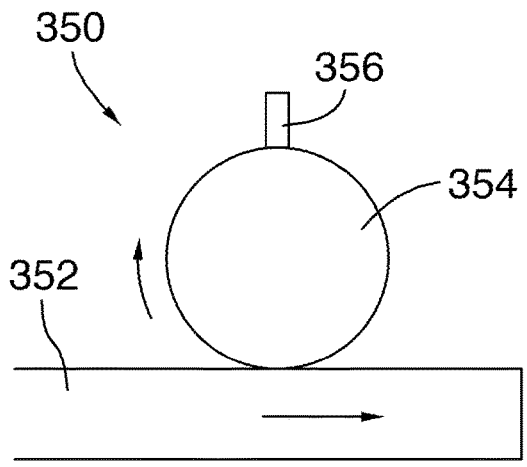
FIGS. 7a and 7b schematically illustrate a mechanical sensor comprising a ball for measuring a displacement and/or a rotation of an elongated instrument, in accordance with an embodiment.
Figure 7B:
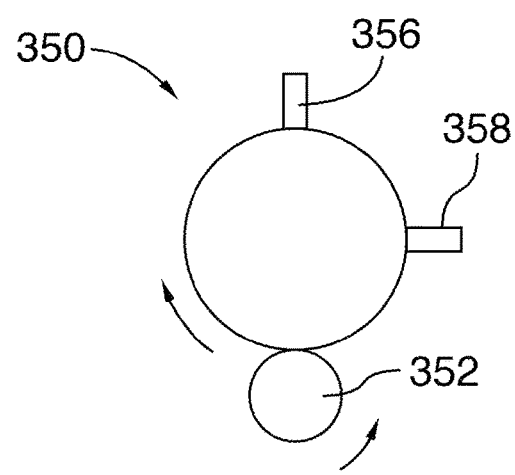

FIGS. 7a and 7b schematically illustrate a first exemplary mechanical sensor unit 350 for measuring both the longitudinal displacement and the rotation of an elongated instrument 352. The sensing unit 350 may be integrated into the sensing module 20, 22. The sensor unit 350 comprises a ball 354 and two rotary sensors 356 and 358. The ball 354 is rotatably secured within the sensor unit 350 so as to rotate about at least two rotation axes. In one embodiment, the ball 354 may rotate in any direction. The rotary sensors 356 and 358 are positioned at different positions around the ball 354 so as to measure the rotation of the ball 354 about two different rotation axes. As illustrated in FIG. 7a, the translation of the elongated instrument 352 along its longitudinal axis triggers the rotation of the ball 354 about a first rotation axis. As illustrated in FIG. 7b, the rotation of the elongated instrument 352 about its longitudinal axis triggers the rotation of the ball 354 about a second and different rotation axis. In the illustrated embodiment, the rotary sensor 356 is positioned so as to measure the rotation of the ball 354 about the first axis caused by the translation of the elongated instrument 352 while the second rotary sensor 358 is positioned to measure the rotation of the ball 354 about the second rotation axis caused by the rotation of the elongated instrument 352 about its longitudinal axis. However, it should be understood that the first and second rotary sensors 356 and 358 may have different positions relative to the ball 354.

In one embodiment, a rotary sensor 356, 358 comprises a roller rotatably secured to the ball 354 so that a rotation of the ball 354 triggers a rotation of the roller, and an encoder such as an optical encoder for measuring the rotation angle of the roller and therefore the rotation of the ball in the direction associated with the roller.

In another embodiment, the rotary sensor 356, 358 comprises an optical sensor for measuring the rotation of the ball 354. For example, the optical sensor may comprise a digital image correlation and tracking sensor, as known in the art.

Figure 8A:
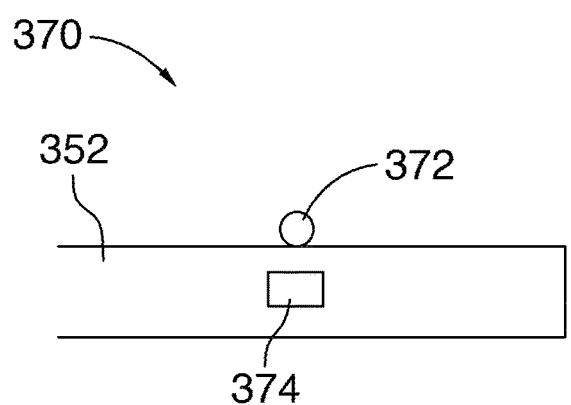
FIGS. 8a and 8b schematically illustrate a mechanical sensor comprising two rollers for measuring a displacement and/or a rotation of an elongated instrument, in accordance with an embodiment.
Figure 8B:
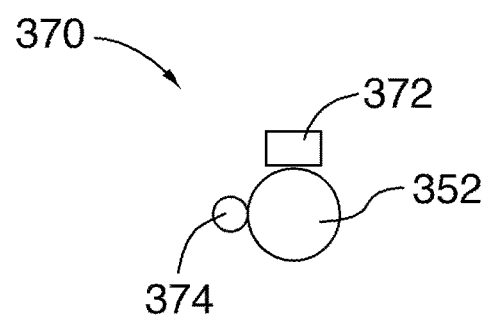

FIGS. 8a and 8b schematically illustrate a second exemplary sensor unit 370 for measuring both the longitudinal displacement and the rotation of an elongated instrument 352. The sensor unit 370 comprises a first roller 372 and a second roller 374 which are each rotatably connected to the elongated instrument 352 so that the rollers 372 and 374 may rotate upon movement of the elongated instrument 352. The first roller 372 is positioned relative to the elongated instrument 352 so that a translation of the elongated instrument 352 along its longitudinal axis triggers a rotation of the roller 372. The second roller 374 is positioned relative to the elongated instrument 352 so that a rotation of the elongated instrument 352 about its longitudinal axis triggers a rotation of the roller 374.

The sensor unit 370 further comprises two encoders each operatively connected to a respective roller 372, 374 in order to measure the rotation of the respective roller 372, 374. The sensor unit 370 further comprises a control unit configured for determining the translation of the elongated instrument 352 and the rotation of the elongated instrument 352 about its longitudinal axis using the rotation angles of the rollers 372 and 374, as known in the art.

In one embodiment, the sensing modules 20, 22 comprises a contactless sensing unit for measuring the displacement of the elongated instrument 12, and optionally the rotation of the elongated instrument 12.

Figure 9:
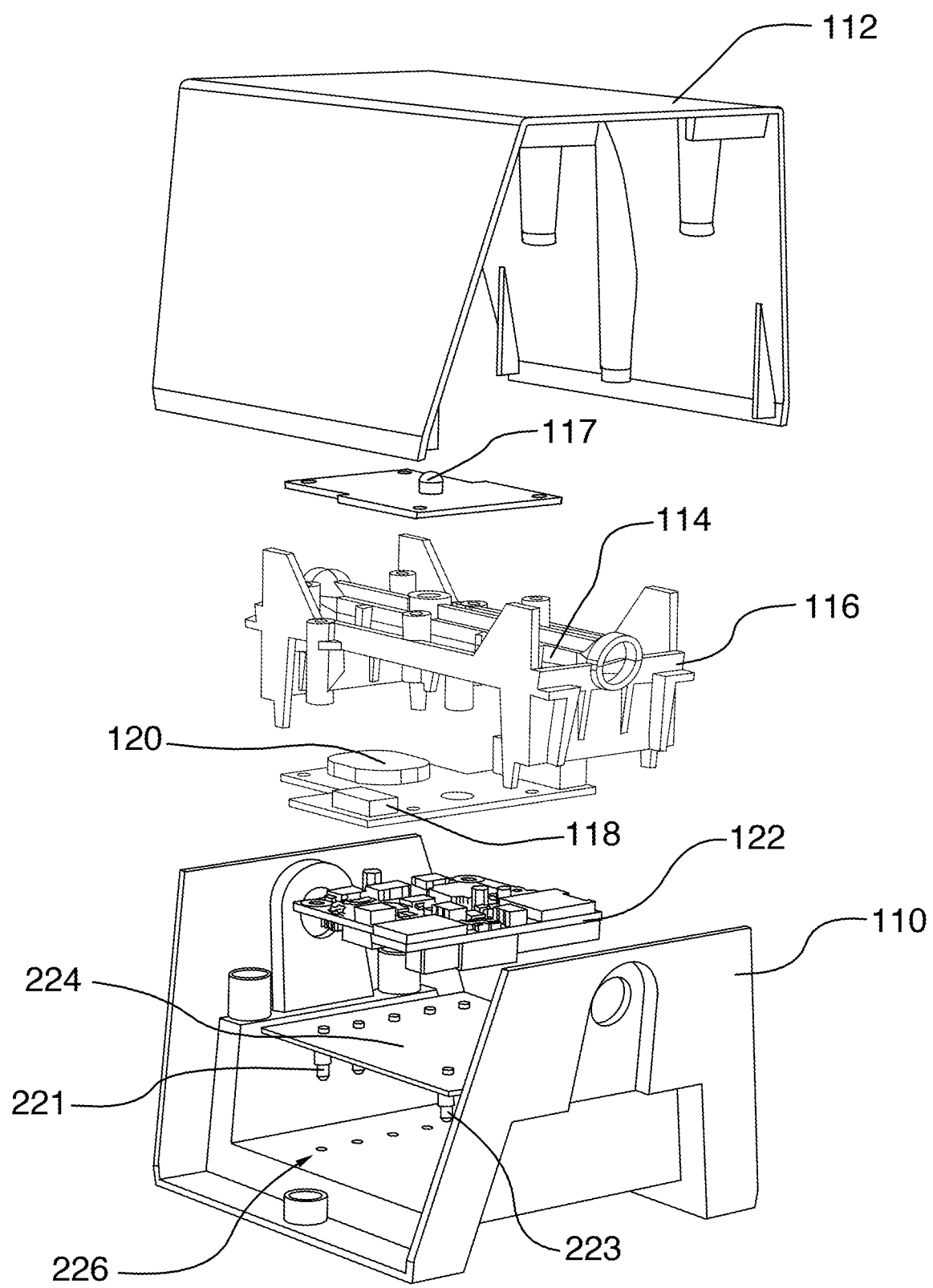
FIG. 9 is a perspective exploded view of a sensing module provided with all optical detection, in accordance with an embodiment.
Figure 10:
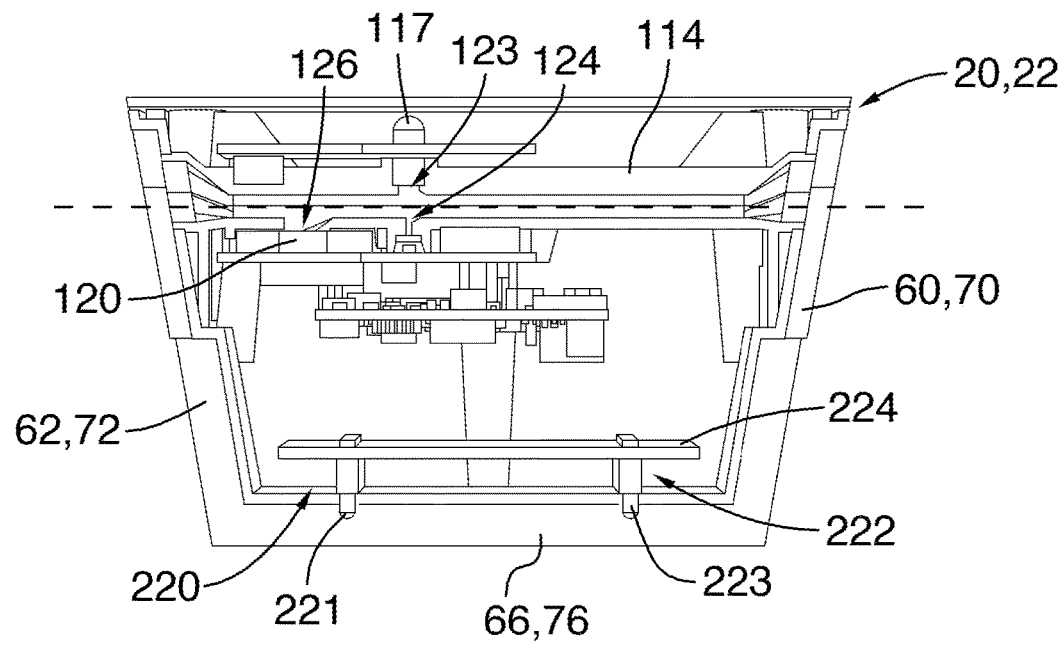
FIG. 10 is a cross-sectional view of the sensing module of FIG. 9.

FIGS. 9 and 10 illustrates one embodiment of a sensing module 20, 22 comprising such as contactless sensing unit. The sensing unit 20, 22 comprises a receiving body 110, a cover 112, a hollow guiding body 114 installed on a cradle 116, a first optical sensor comprising a light source 117 and a light detector 118, a second optical sensor 120 and a control unit 122. The guiding body 114, the cradle 116, the first optical sensor 118, the second optical sensor 120 and the control unit 122 are enclosed within sensing module 20, 22 between the receiving body 110 and the cover 112. The guiding body 114 is a hollow structure which defines a passageway for the elongated instrument. The guiding body 114 may have a tubular shape and is shaped and sized for receiving the elongated instrument 12 therein. The guiding body 114 may be transparent or opaque. The control unit 122 is provided with a processing unit, a memory and communication means.

The guiding body 114 is secured to the cradle 116 which is designed so that when it is positioned within the sensing module 20, 22, the guiding body or tube 116 face the apertures 69, 79 present in the proximal and distal walls of the sensing module 20, 22. The guiding body 114 connects the apertures 69, 79 of the faces 60 and 62, 70 and 72 so that the elongated instrument may cross the module 20, 22.

In one embodiment, one of the two apertures of module 20, 22 may be omitted and the module 20, 22 may then be a stand-alone apparatus.

As illustrated in FIG. 10, the guiding body 114 is provided with first apertures 123 and 124 for allowing the first optical sensor to emit/receive light though the apertures 123 and 124 up to the elongated instrument 12 when in the guiding body 114. The guiding body 114 is further provided with a second aperture 126 for allowing the second optical sensor 120 to sense the elongated instrument 12 when received in the guiding body 114.

It should be understood the optical sensors 118 and 120 are controlled by the control unit 122. It should also be understood that.

The first optical sensor is configured for determining the presence the elongated instrument 12 within the guiding body 114. Upon detection of the presence of the elongated instrument 12, the control unit 122 activates the second optical sensor 120 which is configured for determining the longitudinal displacement of the elongated instrument 12 within the guiding body 114.

In one embodiment, the first optical sensor is further configured for determining the cross-sectional size of the elongated instrument 12, such as its diameter or radius if the elongated instrument 12 is cylindrical or tubular. The control unit 122 compares the measured cross-sectional size to at least one predefined threshold or a predefined range and activates the second optical sensor 120 as a function of the comparison result. Upon positive comparison, the control unit 122 triggers the activation of the second sensor 120.

In one embodiment, if the cross-sectional size of the elongated instrument 12 is contained within the predefined range, then the control unit 122 triggers the activation of the second optical sensor 120 which then determines the displacement of the elongated instrument 12. If the cross-sectional size of the elongated instrument 12 is not contained within the predefined range, then the control unit 122 does not activate the second optical sensor 120 and the displacement of the elongated member 12 is not tracked.

In another embodiment, the control unit 122 triggers the activation of the second optical sensor 120 only if the measured cross-sectional size is greater than a predefined threshold.

In a further embodiment, the control unit 122 triggers the activation of the second optical sensor 120 only if the measured cross-sectional size is less than a predefined threshold.

In one embodiment, the two optical sensors are secured to the cradle 116 and the cradle 116 spring loads the assembly to reduce vibrations and any bending that could affect the measurement of the displacement of the elongated instrument 12.

As described above, the first optical sensor is configured for measuring the cross-sectional size of the elongated instrument inserted into the sensing module 20, 22. In the illustrated embodiment, the first optical sensor comprises the light source 117 and a light detector 118.

It should be understood that the first optical sensor illustrated in FIGS. 9 and 10 is exemplary only and that any adequate optical sensor configured for measuring the cross-sectional dimension of an elongated instrument such as instrument 12 may be used. For example, a camera may be used for determining the cross-sectional dimension of the elongated instrument 12.

Figure 11A:
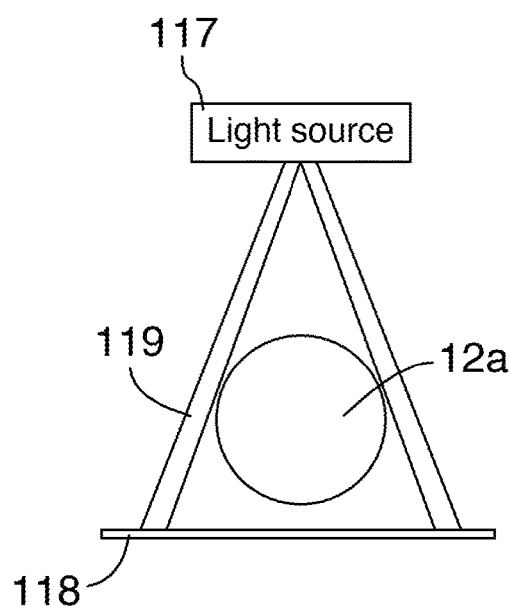
FIGS. 11a and 11b schematically illustrate an optical sensor for determining the diameter of an elongated instrument, in accordance with an embodiment.
Figure 11B:
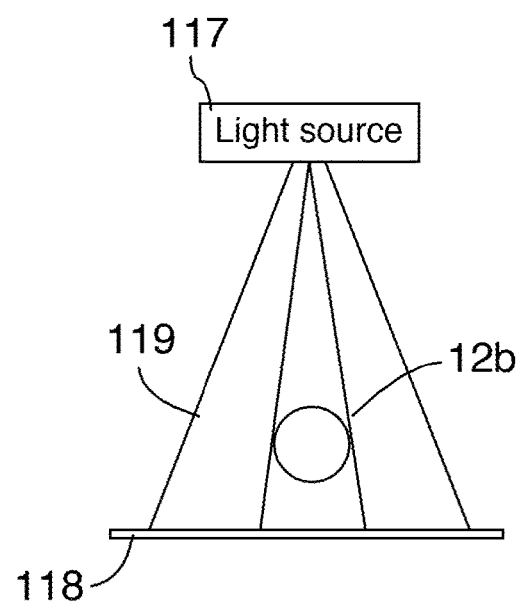

FIGS. 11a and 11b schematically illustrate the principle of operation of the first optical sensor. The light source 117 is positioned on one side of the cradle 116 and the light detector 118 is positioned on the other side of the cradle 116. Both the light source 117 and the light detector 118 face the aperture 124 present in the cradle 116 so that light emitted by the light source 117 may be detected by the light detector 118 when no elongated instrument is present between the light source 117 and the light detector 118. The light detector is adapted to measure the amplitude, intensity or power of the light incident thereon.

As a result, the light source 117 emits a light beam 119 of which at least a portion is incident on the light detector 118. When it is positioned on the cradle 116, an elongated instrument such as elongated instrument 12a block the propagation of at least a portion of the light beam 119 emitted by the light source 117 so that the light detector 118 detects only a portion of the light beam 119 emitted by the light source 117. For example, FIG. 11b illustrates an elongated instrument 12b having a diameter than is less than that of the elongated instrument 12a illustrated in FIG. 11a. As illustrated in FIGS. 11a and 11b, the amount of light reaching the light detector 118 is greater when the small-diameter instrument 12b is inserted between the light source 117 and the light detector 118 in comparison to the scenario where the large diameter instrument 12a is inserted between the light source 117 and the light detector 118.

As illustrated in FIGS. 11a and 11b, the greater the cross-sectional dimension of the elongated instrument is, the less light propagates up to the light detector 118 and the less light intensity is measured by the light detector 118. Therefore, the intensity of the detected light can be related to a given cross-sectional dimension for the elongated instrument. For example, the memory of the module 20, 22 may have stored thereon a database containing light intensity values and corresponding cross-sectional dimensions, or predefined ranges of light intensity values and corresponding cross-sectional dimensions. Therefore, the control unit 122 may receive the measured light intensity from the light detector 118 and retrieves the corresponding cross-sectional dimension. The control unit 122 then uses the retrieved cross-sectional dimension to determine whether the second optical sensor 120 should be activated, as described above.

In one embodiment, a cross-section dimension is represented by a light intensity. In this case, determining the cross-section of an elongated instrument is equivalent to measuring the light intensity when the elongated instrument is located between the light source 117 and the light detector 118. The control unit 122 compares the measured light intensity to a predefined intensity threshold or a range of predefined to identify the elongated instrument.

Regarding the second optical sensor 120, it should be understood that any adequate optical sensor configured for measuring the longitudinal displacement of an elongated instrument and/or the rotation angle of an elongated instrument may be used. For example, digital image correlation and tracking optical sensors may be used. Such a sensor takes successive images of the surface of the elongated instrument and determines the longitudinal displacement and/or rotation from the successive images.

In an embodiment in which the guiding device 114 is transparent, the second optical sensor 120 may comprise at least one camera for imaging the elongated instrument 12 through the guiding device 114 and the control unit 122 is configured for determining the displacement and/or rotation of the elongated instrument 12. An example for such an optical sensor is described in U.S. Pat. Nos. 9,361,808 and 9,361,809.

In one embodiment, the sensing module 20, 22 further comprises comprising a communication unit for transmitting the determined displacement of the elongated instrument 12, and optionally the rotation of the elongated instrument 12. The communication unit may be a wireless communication unit for wirelessly transmitting the data to the simulation computer that will generate the image of the subject comprising the representation of the elongated instrument 12.

While the light detector 118 and the second optical sensor 120 are positioned below the guiding body 114 and the light source 117 is positioned on top of the guiding body 114, it should be understood that other configurations may be possible. For example, the optical sensors 118 and 120 could be positioned elsewhere relative to the guiding body 114. For example, the light detector 118 and the second optical sensor 120 could be positioned on top of the guiding body 114 and the light source 117 could be positioned below the guiding body 114.

In one embodiment, the sensing module 20 and 22 may be configured to determine the displacement of elongated instruments having different cross-sectional sizes. For example, the first sensing module 20 may be adapted to measure the displacement of a first elongated member having a first diameter while the second sensing module 22 may be configured for determining the displacement of a second elongated instrument having a second diameter that is less than the given diameter. In this case, the sensing module 20 is adapted to first determine the diameter of an elongated instrument inserted into the guiding body 114. If the determined diameter corresponds to the first diameter, then the first sensing module 20 measures the displacement of the elongated instrument present in its guiding body 114. However, if the determined diameter does not correspond to the first diameter, then the sensing module 20 does not measure the displacement of the elongated instrument within the guiding body 114.

Similarly, the second sensing module 22 is adapted to first determine the diameter of an elongated instrument inserted into the guiding body 114. If the determined diameter corresponds to the second diameter, then the second sensing module 20 measures the displacement of the elongated instrument translating within its guiding body 114. However, if the determined diameter does not correspond to the second diameter, then the sensing module 20 does not measure the displacement of the elongated instrument within the guiding body 114.

In one embodiment, the guiding body 114 of the sensing module 20, 22 has a cross-sectional dimension that varies along its length in order to prevent elongated instruments having a cross-sectional dimension greater than a predefined dimension from reaching the optical sensors. When the guiding body 114 has a tubular shape, the section of the guiding body 114 adjacent to its longitudinal ends may have a decreasing diameter.

It should be understood that a measured diameter may be considered as corresponding to a predefined diameter such as the first or second diameter when the measured diameter is comprised within a predefined range containing the target diameter. In this case, each sensing unit 20, 22 is configured for measuring the displacement of a respective elongated instrument of which the cross-sectional size is contained with a respective predefined range.

Therefore, when the sensing modules 20 and 22 are configured for tracking the displacement of elongated instruments having different cross-sectional sizes, the apparatus 10 provides the user with flexibility in the design of the apparatus 10. By choosing adequate sensing modules 20 and 22, the user may simulate the insertion of an elongated instrument into different bodies and/or the insertion of elongated instruments having different cross-sectional sizes while using the same modules 14-18.

Figure 12:
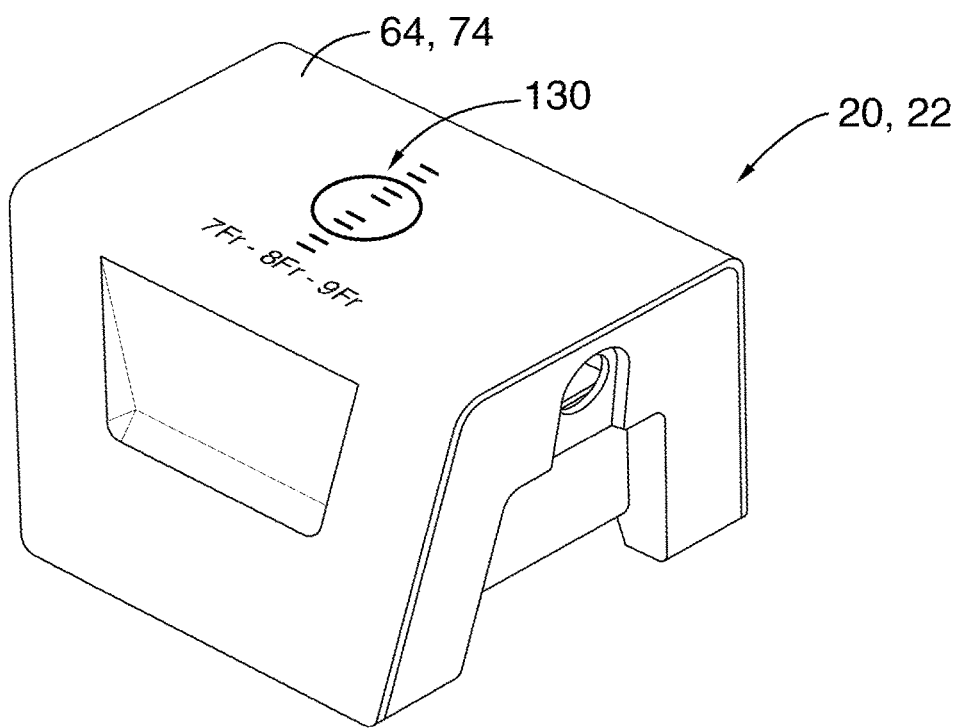
FIG. 12 is a perspective view of a sensing module provided with an identification mark thereon, in accordance with an embodiment.

In an embodiment in which sensing modules are configured for measuring the displacement of elongated instruments having different cross-sectional sizes, the sensing modules may have an indication thereon to differentiate the different sensing modules. For example, an image 130 may be printed or engraved on the top wall 64, 74 of a sensing module 20, 22, as illustrated in FIG. 12.

Figure 13A:
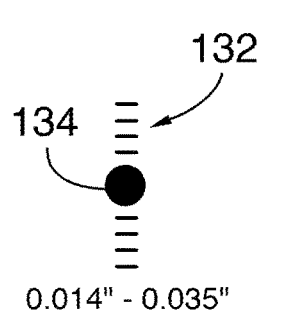
FIGS. 13a-13d each illustrates a respective identification mark for a sensing module, in accordance with an embodiment.
Figure 13B:
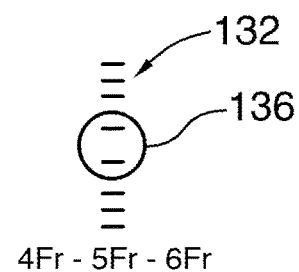
Figure 13C:
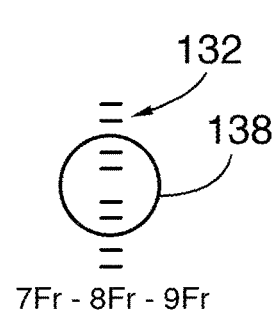
Figure 13D:
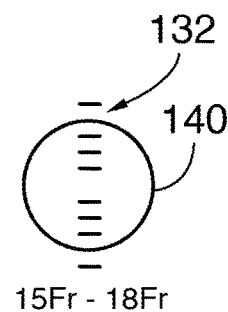

FIGS. 13a-13d illustrates exemplary images that may be used for differentiate the sensing modules as a function of the cross-section size of the elongated instrument that they may detect. The image representing a scale 132 and a dot 134 at the middle of the scale 132 and illustrated in FIG. 13a may be used for identifying sensing modules configured for tracking the displacement of guidewires having a diameter comprised between 0.014" and 0.035". FIG. 13b illustrates an image representing the scale 132 and a circle 136 having a first diameter, which may be used for identifying sensing modules configured for tracking the displacement of lead wires having a diameter comprised between 4 Fr and 6 Fr. FIG. 13c illustrates an image representing the scale 132 and a circle 138 having a second diameter greater than the first diameter, which may be used for identifying sensing modules configured for tracking the displacement of catheters having a diameter comprised between 7 Fr and 9 Fr. FIG. 13d illustrates an image representing the scale 132 and a circle 140 having a third diameter greater than the second diameter, which may be used for identifying sensing modules configured for tracking the displacement of delivery tubes having a diameter comprised between 15 Fr and 18 Fr, for example.

Figure 14:
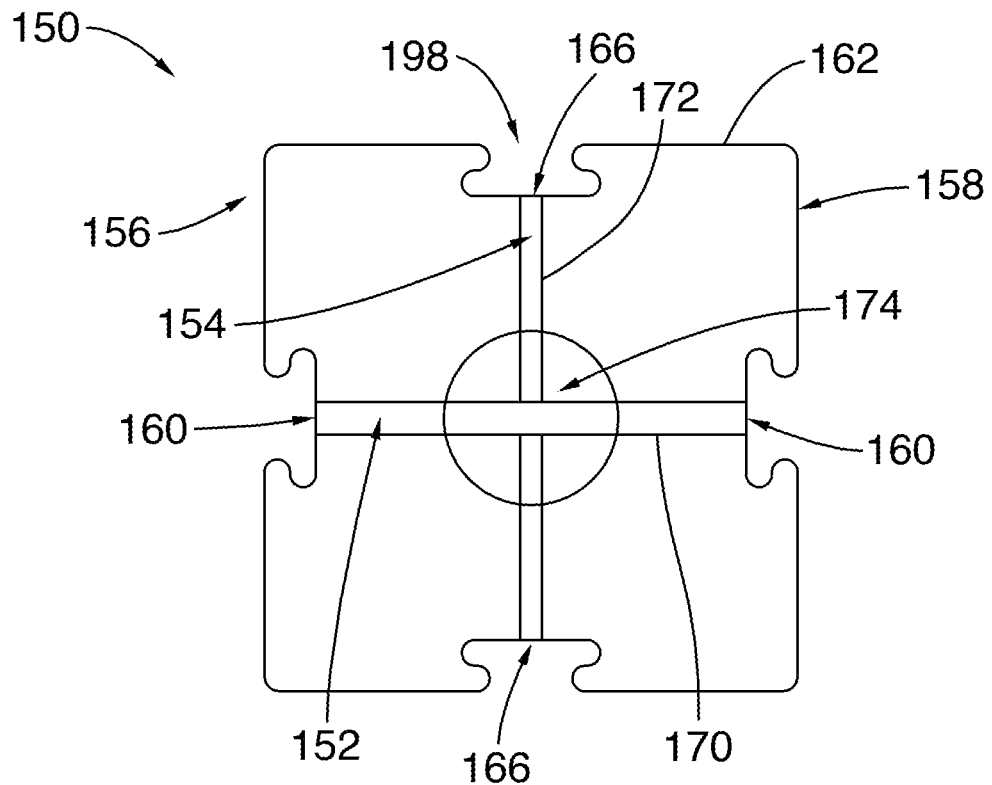
FIG. 14 is a cross-sectional view of a cross-channel medical apparatus comprising two passageways for different elongated instruments, in accordance with an embodiment.

While in the above description, a sensing module 20, 22 comprises a single passageway defined between the two apertures 69, 79, FIG. 14 illustrates a sensing module 150 which can be used for tracking the displacement of elongated instruments having different cross-sectional sizes. In the illustrated embodiment, the sensing module 150 comprises a frame having a substantially cubic shape and defining two different passageways 152 and 154 for elongated instruments having different cross-sectional sizes. The frame comprises two sets of lateral faces extending between a top face and a bottom face. The first set of lateral faces comprises the opposite faces 156 and 158 each provided with a respective aperture 160. The aperture 160 has a first dimension for receiving therein elongated instruments having a cross-sectional size at most equal to the dimension of the aperture 160.

The second set of lateral faces comprises the opposite faces 162 and 164 each provided with a respective aperture 166. The aperture 160 has a second dimension different form the first dimension of the aperture 160, for receiving therein elongated instruments having a cross-sectional size at most equal to the second dimension of the aperture 166. In the illustrated embodiment, the dimension of the aperture 160 is greater than that of the aperture 166 so that the passageway 152 may receive elongated instruments having a greater cross-sectional dimension than that of the elongated instruments that may be received in the passageway 154.

In one embodiment and as illustrated in FIG. 14, the position of the apertures 160 and 166 within their respective face 156, 158 and 162, 164 is chosen so that the passageways 152 and 154 intersect one another. Indeed, the centers of the two apertures 160 and the centers of the two apertures 166 are coplanar, i.e. the four centers belong to a same plane. In this case, the sensing module 150 may comprise a single sensing unit for measuring the displacement and/or rotation of an elongated instrument within the passageway 152 or the passageway 154. The sensing unit is positioned adjacent to the intersection of the passageways 152 and 154. For example, the sensing unit may be positioned on top of the intersection between the passageways 152 and 154. In another example, the sensing unit may be positioned below the intersection between the passageways 152 and 154.

In one embodiment, the sensing module 150 further comprises a hollow guiding body 170 extending between the lateral faces 156 and 158 within the frame of the sensing module 150. The guiding body 170 is aligned with the apertures 160 present in the faces 156 and 158 so that an elongated member may be introduced into the guiding body 170 via one of the apertures 160. The sensing module 150 further comprises a hollow guiding body 172 extending between the lateral faces 162 and 164 within the frame of the sensing module 150. The guiding body 172 is aligned with the apertures 166 present in the faces 162 and 164 so that an elongated member may be introduced into the guiding body 172 via one of the apertures 166. The two guiding structures 170 and 172 intersect each other at an intersection zone 174 and the sensing unit for is positioned at the intersection zone/point so as to measure the displacement of an elongated instrument moving in the guiding body 170 or 172, and optionally the rotation of the elongated instrument.

It should be understood that the sensing unit contained in the sensing module 150 may be any adequate sensor configured for measuring the longitudinal displacement and/or rotation of an elongated instrument inserted into one of the two passageways. For example, the sensing unit may be a mechanical sensor such as one of the mechanical sensor presented above. In another example, the sensing unit may be an optical sensor such as one of the optical sensors presented above.

In one embodiment, the guiding body 170, 172 comprises a plate extending between the faces 156 and 158, 162 and 164. The plate may be provided with rails extending between the faces 156 and 158, 162 and 164 on opposite lateral sides thereof. In this case, the sensing unit may be positioned on top of the intersection of the two guiding bodies 170 and 172.

In one embodiment, the apertures 160 and 166 are circular. In this case, the diameter of the apertures 160 is larger than that of the apertures 166. In this case, the guiding bodies 170 and 172 may each have a tubular shape. In this case, an aperture may be present in the guiding bodies 170 and 172 at the intersection thereof to allow the sensing unit measuring the displacement and/or rotation of an elongated instrument moving in the guiding body 170 or 172. For example, the aperture may be present on the top of the guiding bodies 170 and 172. In this case, the sensing unit is positioned on top of the intersection point of the guiding bodies 170 and 172. In another embodiment, the aperture may extend on the bottom portion of the guiding bodies 170 and 172 at an intersection thereof and the sensing unit is positioned below the intersection point between the guiding bodies 170 and 172.

It should be understood that the sensing module 150 may be provided with at least a processing unit and a communication unit for transmitting to a simulation computer the measured displacement and/or rotation of the elongated instrument.

Figure 15:
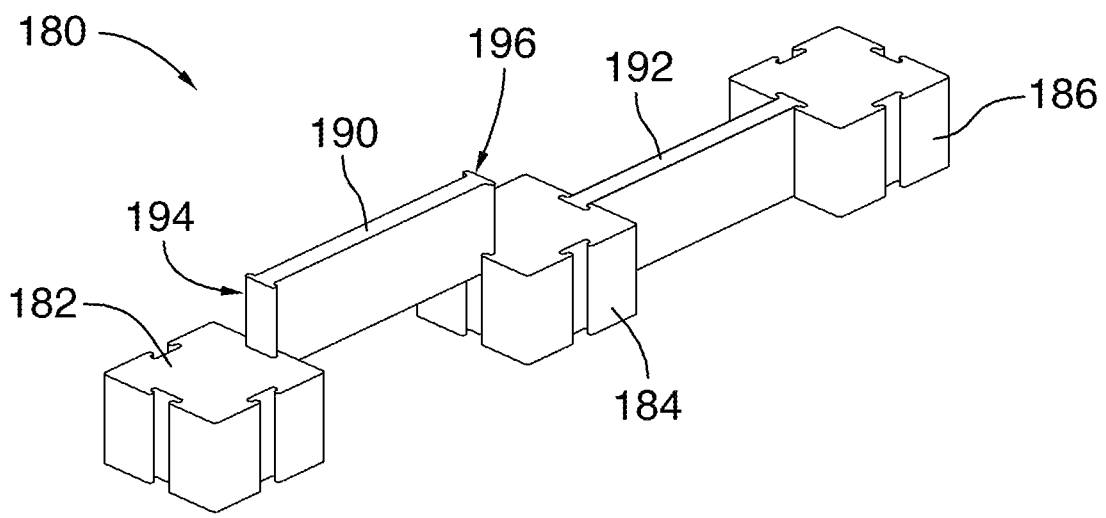
FIG. 15 illustrates a modular system for simulating the insertion of an elongated instrument into a subject, the modular system comprising three cross-channel sensing modules, in accordance with an embodiment.

In one embodiment, the sensing module 150 may be used in a modular apparatus for simulating the insertion of an elongated instrument within a subject. FIG. 15 illustrates one embodiment of a modular apparatus 180 comprising three sensing modules 182, 184 and 186 and two intermediary modules 190 and 192. Each sensing module 182, 184, 186 may be similar to sensing module 150 and be provided with two passageways that intersect each other, have different size and extend between different faces.

The intermediary module 190, 192 is similar to the intermediary module 16 and comprises a frame that extends between two opposite end faces 194 and 196 along a longitudinal axis. Each end face 194 and 196 is provided with an aperture (not shown) sized and shaped for receiving therein the elongated instrument.

It should be understood that the position of the apertures on the faces of the sensing modules 182-186 and that of the apertures 194 and 196 on the end faces of the intermediary modules 190 and 192 are chosen so as to all be aligned along an axis when the intermediary modules 190 and 192 and the sensing modules 182, 184 and 186 are removably securable together, and thereby allow the elongated instrument to be moved through all of the modules.

The intermediary modules 190 and 192 and the sensing modules 182, 184 and 186 are removably securable together. It should be understood that any adequate securing means adapted to allow a removable connection between a sensing unit and an intermediary module may be used.

In the illustrated embodiment, each end face 194, 196 of an intermediary module 190, 192 is provided with a T-shaped protrusion while each lateral face of the sensing module 182, 184, 186 is provided with a mating T-shaped recess such as recess 198 illustrated in FIG. 14. A given intermediary module 190, 192 is removably secured to a given face of a sensing module 182, 184, 186 by inserting a T-shaped protrusion of the given intermediary module 190, 192 into a T-shaped recess of the given face of the given module 182, 184, 186.

It should be understood that the number of sensing modules 182, 184, 186 and the number of intermediary modules 190 and 192 may vary as along as the modular apparatus 180 comprises at least one sensing module and at least one intermediary module.

The person skilled in the art will understand that the modular apparatus 180 allows simulating the insertion of the elongated instruments having different cross-sectional dimensions such as different diameters while using the same sensing modules.

In another embodiment, the sensing module 150 may be a stand-alone apparatus for simulating the insertion of an elongated instrument into a body. In this case, the sensing module 150 may be referred to as the sensing device 150 and the T-shaped recess present on each face 156, 158, 162, 164 may be omitted. The dimension and shape of the sensing device 150 may be varied according to a desired range of translation for the elongated instrument.

Figure 16:
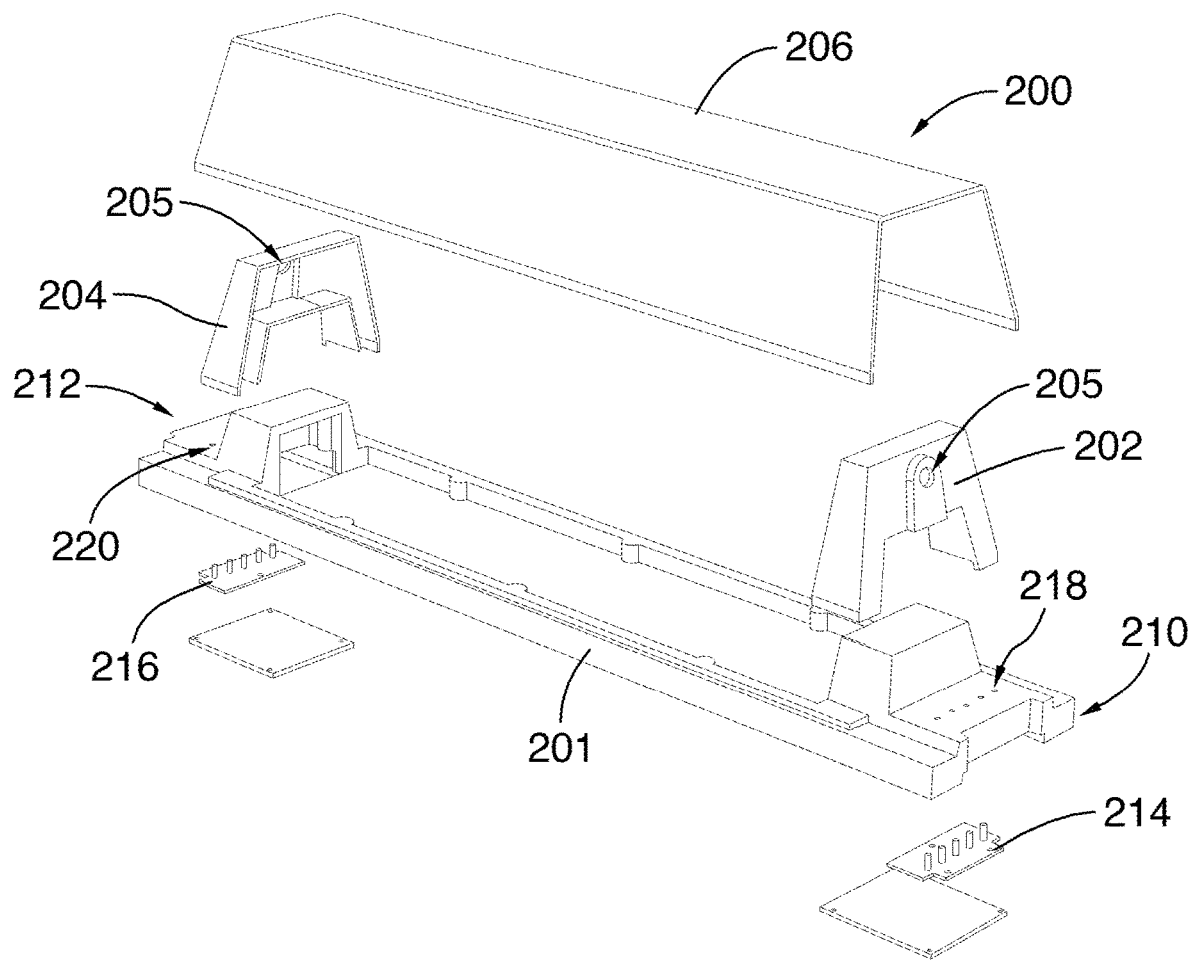
FIG. 16 is a perspective exploded view of an intermediary module, in accordance with an embodiment.
Figure 17:
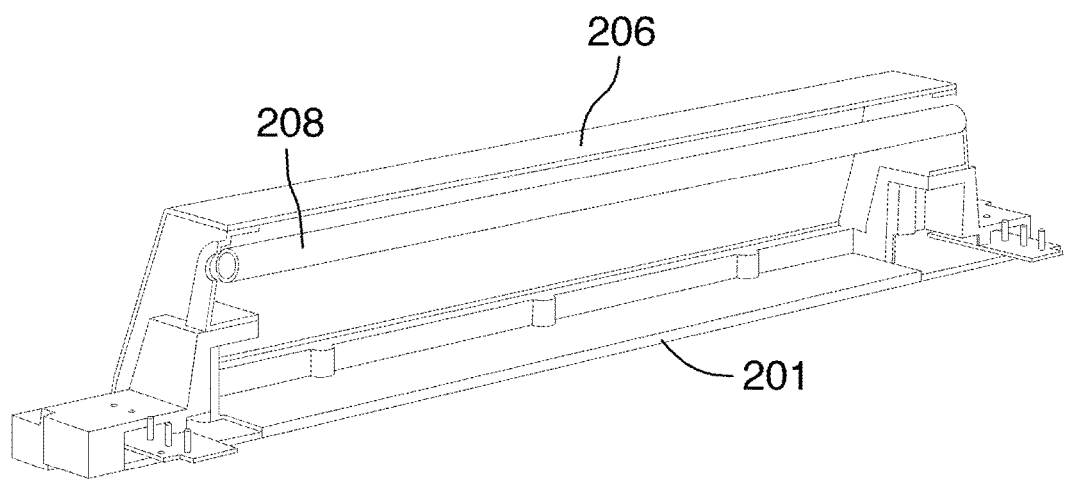
FIG. 17 is a cross-sectional view of the intermediary module of FIG. 16.

FIGS. 16 and 17 illustrate an intermediary module 200 that may be used in the modular apparatus 10. The intermediary module 16 comprises a base plate 201, two end walls 202 and 204 each provided with a respective aperture 205, a cover 206 and a tubular body 208. The base plate 201 extends along a longitudinal axis between two opposite ends 210 and 212. The end wall 202 projects transversely from the base plate 201 adjacent to the end 210 of the base plate 201 and the end wall 204 projects transversely from the base plate 201 adjacent to the end 212 of the base plate 201.

The tubular body 208 has an internal diameter that is equal to or greater than the diameter of the apertures 205. The tubular body 208 extends from the end wall 202 to the end wall 204 and is positioned so that the centers of the apertures 205 are located on the symmetry axis of the tubular body 208. As a result, when it is inserted through one of the two apertures 205, an elongated instrument is received within the tubular body 208 and translate inside the tubular body 208 up to the other aperture 205.

In one embodiment, the intermediary module 200 is provided with two electrical pin connectors 214 and 216 for allowing communication within the modular apparatus in which it is used, such as modular apparatus 10. In this case, the section of the base plate 201 adjacent to the end 210 thereof comprises a plurality of holes 218 extending through a thickness thereof and the section of the base plate 201 adjacent to the end 212 is provided with a plurality of holes 220 extending through a thickness thereof. The holes 218 are sized and shaped to each receive a respective pin of the pin connector 214 while the holes 220 are sized and shaped to each receive a respective pin of the pin connector 216. It should be understood that the connectors 214 and 216 are electrically connected together so that data may be transmitted form the connector 214 to the connector 216 and vice versa.

In one embodiment, a sensing module is provided with two connectors each configured to be connected to the connector of another module upon removable securing of the sensing module to the other module. For example, a sensing module may be provided with two pin connectors each connectable to a respective pin connector 214, 216 upon removable connection between the sensing module and the intermediary module 200.

Referring back to FIGS. 9 and 10, the sensing module 20, 22 comprises a first pin connector 220 comprising at least one pin 221 and a second pin connector 222 comprising at least one pin 223. The pins 221 and 223 are secured to a plate 224 and extend downwardly therefrom. The bottom wall 66, 76 comprises at least one hole (not shown) extending therethrough adjacent to the wall 60, 70. Each hole is shaped and sized for receiving therein a respective pin 223. When the pins 223 are inserted into their respective hole, each pin 223 slightly projects form the bottom wall 66, 76. The bottom wall 66, 76 further comprises at least one hole 226 extending therethrough adjacent to the wall 62, 72. Each hole 226 is shaped and sized for receiving therein a respective pin 221. When the pins 221 are inserted into their respective hole 226, each pin 223 slightly projects form the bottom wall 66, 76.

When the sensing module 20, 22 is removably connected to the module 200 for example, the pins 221 of the pin connector 220 are then each in physical contact with a respective pin of the pin connector 216 for example. Information may then be transmitted from the sensing module 20, 22 to the module 200 and vice versa.

Figure 18:
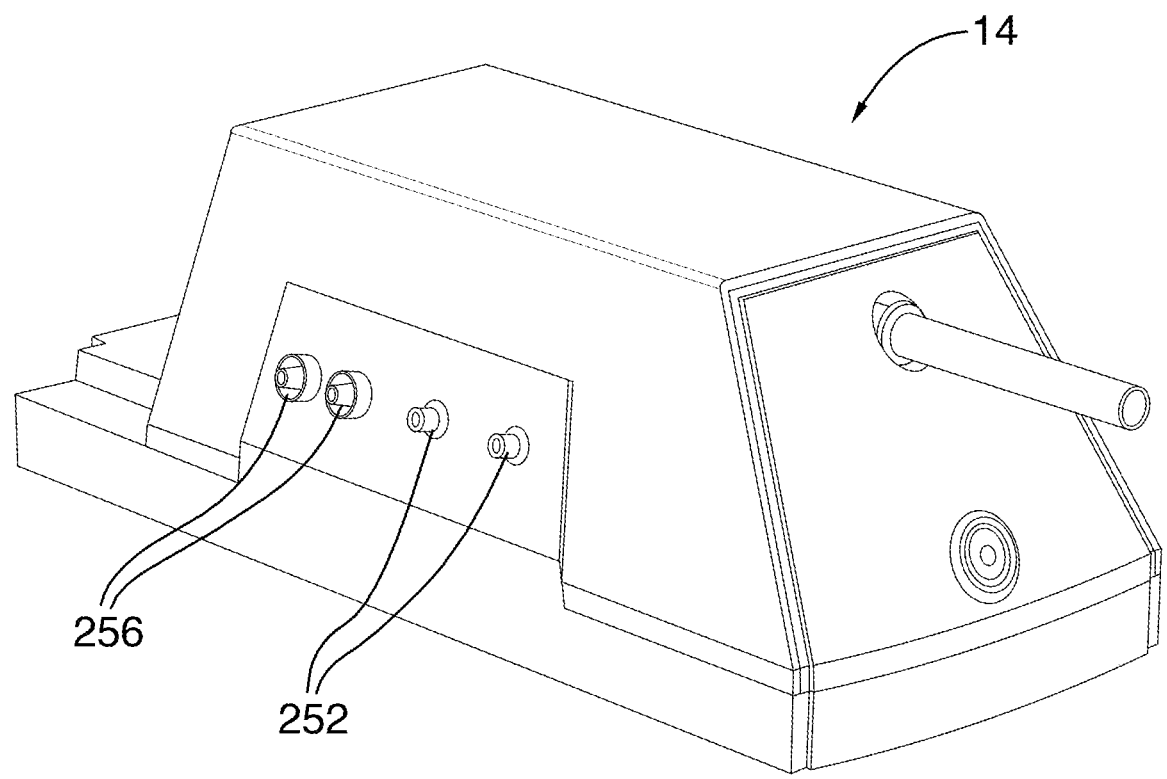
FIG. 18 is a front perspective view of a proximal module, in accordance with an embodiment.
Figure 19:
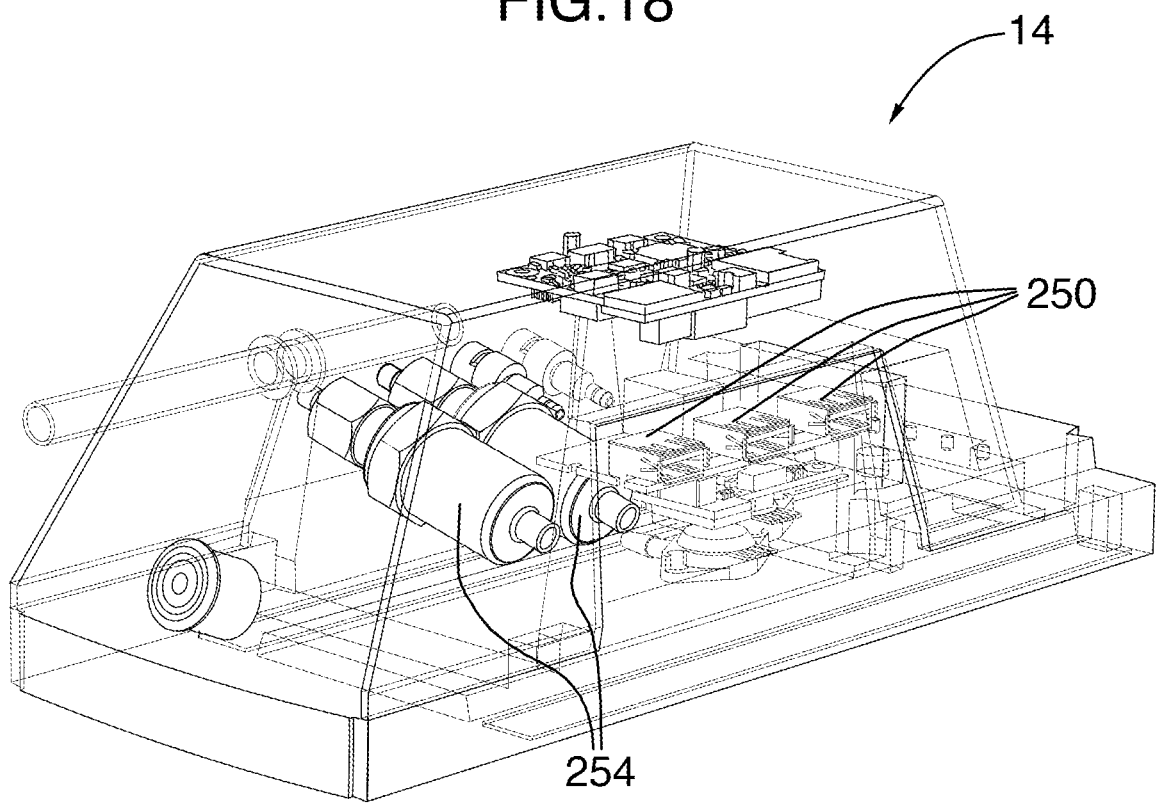
FIG. 19 is rear perspective view of the proximal module of FIG. 18 with the frame made transparent.

FIGS. 18 and 19 illustrates one embodiment of a proximal module 14 provided with a processing unit, a memory and a communication unit. The processing unit receives the information collected by the sensing modules 20 and 22 and transmits the collected information to the simulation computer. In the illustrated embodiment, the proximal module 14 is provided with USB ports 250 for communicating with the simulation computer machine. The proximal module 14 is further provided with a human-machine interface for simulating the injection of air for inflating a balloon and the injection of contrast agent. The proximal module 14 comprises two ports 252 for connecting thereto a contrast delivery system and two pressure sensors 254 each connected to a respective port 252 for measuring the pressure of the contrast agent. The proximal module is further provided with two ports 256 for connecting thereto a gas delivery system.

It should be understood that the above described modules 14, 16 and 18 may each be provided with an internal tubular body such as tubular body 208 for guiding the elongated instrument when inserted therein.

It should also be understood that the number of sensing units and the number other modules may vary as long as the apparatus comprises at least one sensing module and at least another embodiment such as a proximal module, a distal module or an intermediary module.

Figure 20:
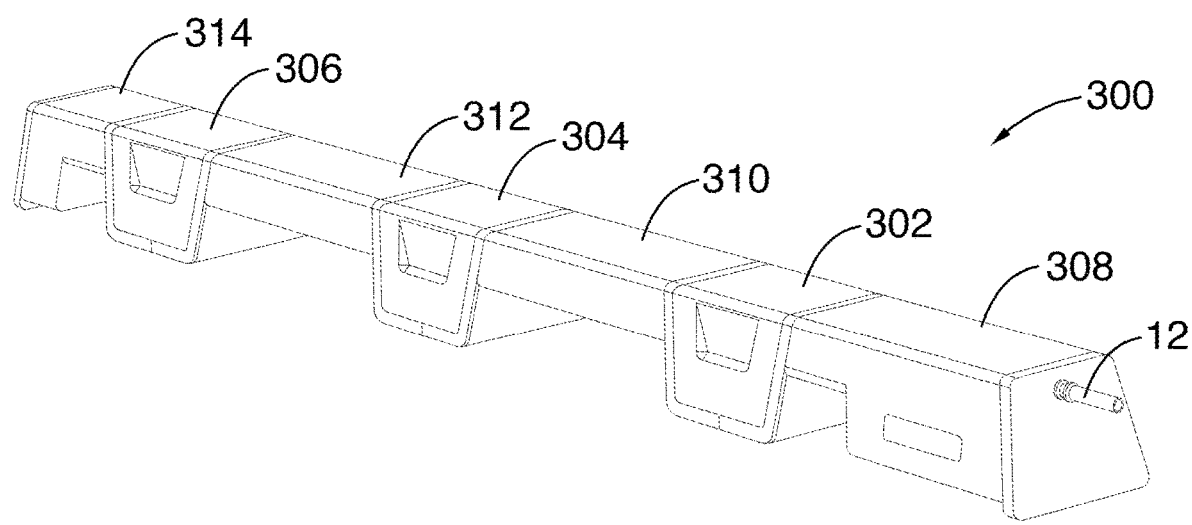
FIG. 20 is a perspective view of a modular medical apparatus for simulating the insertion of an elongated instrument into a subject, the modular medical apparatus comprising a proximal module, a distal module, three sensing modules and two intermediary modules removably secured together, in accordance with an embodiment.

For example, the modular apparatus 300 illustrated in FIG. 20 comprises three sensing modules 302, 304 and 306, a proximal module 308, two intermediary modules 310 and 312 and a distal module 314. The first sensing module 302 is removably inserted between the proximal module 308 and the first intermediary module 310. The second sensing module 304 is removably secured between the first and second intermediary modules 310 and 312 while the third sensing module 306 is removably inserted between the second intermediary module 312 and the distal module 314.

It should be understood that the length of the modules may vary to simulate different bodies.

It should be understood that a subject refers to a human being, an animal or the like, or a part thereof.

The embodiments of the invention described above are intended to be exemplary only. The scope of the invention is therefore intended to be limited solely by the scope of the appended claims.

We claim:

1. An apparatus for simulating an insertion of an elongated instrument into a subject, comprising:

a frame defining an enclosure, the frame extending between two end walls along a first axis and two lateral walls along a second axis, one of the two end walls being provided with an insertion aperture and one of the two lateral walls being provided with an insertion hole, the insertion aperture defining a first passageway within the frame for the elongated instrument and the insertion hole defining a second passageway within the frame for the elongated instrument, the first and second passageways intersecting each other at an intersection point; and a sensor contained within the frame and configured for measuring at least one of a displacement of the elongated instrument and a rotation of the elongated instrument, the sensor being positioned adjacent to the intersection point for performing the measurement of the at least one of the displacement and the rotation at the intersection point.

2. The apparatus of claim 1, wherein the insertion aperture and the insertion hole have different sizes for receiving therein elongated instruments having different cross-sectional dimensions.

3. The apparatus of claim 1, further comprising a first guiding structure extending from the insertion aperture along the first passageway for receiving and guiding the elongated instrument inserted through the insertion aperture, and a second guiding structure extending from the insertion hole along the second passageway for receiving and guiding the elongated instrument inserted through the insertion hole.

4. The apparatus of claim 3, wherein the first guiding structure comprises a first hollow guiding device for receiving the elongated instrument therein and the second guiding structure comprises a second hollow device for receiving the elongated instrument therein.

5. The apparatus of claim 4, wherein the first hollow guiding device comprises a first tube and the second hollow guiding device comprises a second tube.

6. The apparatus of claim 4 or 5, wherein the first and second hollow guiding devices are transparent.

7. The apparatus of claim 6, wherein the sensor comprises at least one camera for imaging the elongated instrument at an intersection of the first hollow guiding device and the second hollow guiding device, the sensor being further configured for determining the at least one of the displacement and the rotation using images taken by the at least one camera.

8. The apparatus of claim 4, wherein the first hollow guiding device comprises a first aperture and the second hollow guiding device comprises a second aperture, the first and second apertures forming a sensing aperture located at an intersection between the first hollow guiding device and the second hollow guiding device.

9. The apparatus of claim 8, wherein the sensor comprises at least one optical sensor for measuring the at least one of the displacement and the rotation of the elongated instrument.

10. The apparatus of claim 9, wherein the at least one optical sensor comprises at least one digital image correlation and tracking sensor.

11. The apparatus of claim 8, wherein the sensor comprises at least one mechanical sensor for measuring the at least one of the displacement and the rotation of the elongated instrument.

12. The apparatus of claim 11, wherein the at least one mechanical sensor comprises a ball rotatably engageable with the elongated instrument and two rotary sensors each for measuring a rotation of the ball about a respective rotation axis.

13. The apparatus of claim 12, wherein each one of the two rotary sensors comprises a roller rotatably connected to the ball and an encoder for measuring a rotation of the roller.

14. The apparatus of claim 12, wherein each one of the two rotary sensors comprises an optical sensor.

15. The apparatus of claim 14, wherein each optical sensor comprises a digital image correlation and tracking sensor.

16. The apparatus of claim 11, wherein the at least one mechanical sensor comprises two rollers each rotatably engageable with the elongated instrument and two encoders each for measuring a rotation of a respective one of the two rollers.

* * * * *